(12) United States Patent
Simon

(10) Patent No.: US 6,569,866 B2
(45) Date of Patent: May 27, 2003

(54) SUSTAINED-RELEASE NALMEFENE PREPARATIONS AND METHOD

(76) Inventor: David Lew Simon, P.O. Box 618, Mansfield Center, CT (US) 06250

( * ) Notice: Subject to any disclaimer, the term of this patent is extended or adjusted under 35 U.S.C. 154(b) by 0 days.

(21) Appl. No.: 09/922,873

(22) Filed: Aug. 6, 2001

(65) Prior Publication Data

US 2002/0037313 A1 Mar. 28, 2002

Related U.S. Application Data

(63) Continuation of application No. 09/152,834, filed on Sep. 14, 1998, now Pat. No. 6,271,240, which is a continuation-in-part of application No. 08/866,334, filed on May 30, 1997, now abandoned, and a continuation-in-part of application No. 08/643,775, filed on May 6, 1996, now abandoned.

(51) Int. Cl.$^7$ ............................................. A61K 31/44
(52) U.S. Cl. ...................... 514/282; 514/281; 514/410; 424/449
(58) Field of Search ..................... 424/449; 514/410, 514/282, 281

(56) References Cited

U.S. PATENT DOCUMENTS 4,626,539 A  *  12/1986  Aungst et al. .............. 514/282
5,512,593 A  *   4/1996  Dante et al. ................ 514/410

* cited by examiner

Primary Examiner—Dwayne C. Jones
(74) Attorney, Agent, or Firm—Pillsbury Winthrop

(57) ABSTRACT

A nalmefene transdermal delivery system useful for the treatment of human patients suffering from opioid addiction.

21 Claims, 1 Drawing Sheet

SUSTAINED-RELEASE NALMEFENE PREPARATIONS AND METHOD

RELATED APPLICATIONS

Figure 1:
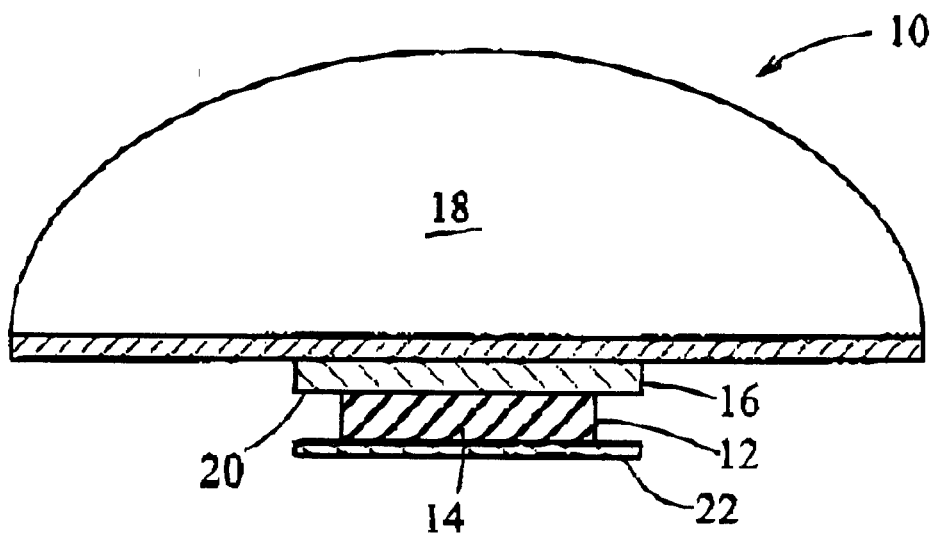

This patent application is a continuation application of U.S. patent application Ser. No. 09/152,834, filed Sep. 14, 1998, now U.S. Pat. No. 6,271,240, which is a continuation-in-part of U.S. patent application Ser. No. 08/866,334, filed May 30, 1997, abandoned on May 12, 1998, and U.S. patent application Ser. No. 08/643,775, filed May 6, 1996, abandoned on Sep. 22, 1998, the disclosure of each which is hereby incorporated by reference.

FIELD OF THE INVENTION

The present invention relates to novel methods for treating humans addicted to opioid agonist analgesics. In particular, the invention relates to methods for prolonged administration of nalmefene following opioid detoxification, and administration of a medication that increases dopamine in the central nervous system, such as bupropion, in conjunction with the administration of nalmefene.

BACKGROUND OF THE INVENTION

An opioid agonist analgesic is a drug or pharmaceutical agent that traditionally is used to treat pain, to suppress coughing, to treat diarrhea, and for other medicinal uses. Depending upon the degree with which a particular opioid agonist medication binds to specific opioid receptor subtypes, such as its affinity for one opioid subtype receptor in preference to another, the opioid agonist analgesic may tend to cause euphoria, or it may tend to cause dysphoria. Some opioid analgesic agonists may also tend to cause nausea by stimulating or inhibiting areas in the brain known as "the vomiting center" and "the chemotactic zone," depending upon the degree with which specific opioid receptor subtypes are activated, and depending to some extent upon the ability of a particular opioid agonist analgesic to penetrate the blood-brain-barrier (BBB). Examples of opioid receptor subtypes are delta-receptors, kappa-receptors, mu-receptors and sigma receptors. These opioid receptor subtypes may be further subcategorized, as for example, $mu_1$-receptors and $mu_2$-receptors.

The opioid antagonist nalmefene has unique characteristics which set it apart from other opioid antagonists such as, for example, naloxone and naltrexone. The unique opioid receptor subtype binding profile of nalmefene enables nalmefene alone, as compared to naloxone and naltrexone, to allow preferred antagonism of opioids at the kappa-opioid receptors versus the mu-opioid receptors, which in turn results in an optimal homeostatic balance of dopamine.

Szekely shows a schematic representation of two opposing opioid systems located in the mesolimbic system of the human central nervous system. These systems modulate A10 dopaminergic neurons projecting in the nucleus accumbens. As illustrated in this reference, stimulation of mu-opioid receptors (the mu subtype of opioid receptor) in the ventral tegmental area (VTA), the site of origin of the A10 neurons, increases dopamine release in the nucleus accumbens (NA). Selective blockade of this mu-receptor results in significant decrease in dopamine release in the nucleus accumbens. In stark contrast, stimulation of kappa-receptors (the kappa subtype of opioid receptor) in either the VTA or the NA results in a decrease in the amount of dopamine released. Selective blockade of kappa-receptors significantly increases dopamine release.

Spanagel et al. demonstrate that tonically active and functionally opposing mu and kappa opioid systems regulate mesolimbic dopamine release in the nucleus accumbens. They report that the injection of mu-opioid agonists such as DAGO into the VTA stimulate mu-opioid receptors and increase the release of dopamine from the VTA into the NA. As would be expected, administration of a mu-opioid receptor antagonist into the VTA decreases dopamine release. The authors further report that kappa-opioid receptors agonists such as U-6953 infused into the NA inhibit dopamine release there, whereas kappa-opioid receptor antagonists such as nor-BNI increase dopamine release. An "agonist" is a "like" chemical with similar action to a given drug. An "antagonist" is a chemical, often with a similar chemical structure to a given drug, which exerts a dissimilar action to the given drug, in general preventing the "like" action of that given drug. With opioid receptors, in general, an agonist binds to the receptor and activates it in such a way as to begin a cascade of chemical or pharmacological events so as to result in the end effect related to a particular opioid receptor subtype. In contradistinction, an antagonist will bind to the receptor but not activate it. An antagonist exerts its actions by blocking the receptors from agonists, by physically occupying the space on the receptor where an agonist would otherwise bind.

The opposing mu and kappa opioid systems acting together provide a homeostasis of dopamine levels within the central nervous system. Changes in these opioid systems, such as by activation or blockade of the specific receptors, would therefore be expected to modulate opioid-induced effects that are mediated by mesolimbic pathways. Mu and kappa receptors are found elsewhere in the human body. For example, they have been located in the spinal cord (See Fujimoto, Bakshi and Behrmann, below) and in other non-central nervous system organs such as the kidney and intestine (See Ohnishi and Kreek, below). Accordingly, the model presented provides a neurochemical framework for understanding the adaptive changes resulting from long term use of opioids, as well as the clinical response elicited by exogenously administered opioid agonists and antagonists having different binding profiles.

For example, Pan et al report modifications in opioid-induced behavior resulting from changes in these mu and kappa systems. These authors state that the effects of opposing mu and kappa receptors extend to opioid action on emotion, perception and drug reinforcement. While morphine and other mu-opioid agonists increase dopamine release and produce euphoria and place preference, kappa-opioid agonists reduce mesolimbic dopamine release and produce dysphoria and aversion.

Scientists have shown that nalmefene, relative to other opioid antagonists such as naloxone and naltrexone, is significantly more kappa-receptor preferring. By way of example, Kreek et al. conclude that nalmefene has more kappa binding activity than either naloxone or naltrexone. Specifically, nalmefene is more potent than either naloxone or naltrexone as a kappa-receptor antagonist, and therefore would block kappa agonists (e.g. the naturally occurring dynorphin) to a greater extent than the other antagonists.

Fujimoto et al. demonstrate differences between mu and kappa receptor effects in the spinal cord. Specifically, these authors report that the administration of dynorphin, a potent kappa agonist, results in decreased analgesia. The dynorphin causes antianalgesic effects at the level of the spinal cord. Fujimoto shows that when a kappa-opioid receptor antagonist such as Cholera Toxin is given, the antianalgesic effect of dynorphin is inhibited.

Bakshi et al. shows that kappa receptors are widely distributed in the spinal cord, and that administration of dynorphin causes motor impairment. These authors also demonstrate that nalmefene is selective for these intraspinal kappa receptors, and limits dynorphin induced motor dysfunction after spinal cord injury.

Behrmann et al. report that a single dose of nalmefene has increased activity at kappa receptors and that a single dose of nalmefene exerts a significant neuroprotective effect after acute spinal cord injury, in direct contrast to the mu-preferring opioid antagonist naloxone that showed no significant effect on neurological recovery after spinal cord injury.

Ohnishi et al. teach the effects on urine production due to kappa-opioid receptor pharmacology at both the level of the pituitary gland and the kidney.

Crain et al. (U.S. Pat. No. 5,580,876) teach a method for "selectively enhancing the analgesic potency of a bimodally-acting opioid agonist" which shows that nalmefene, much more so than other opioid antagonists, enhances analgesia produced by opioid agonist analgesics. Crain et al. further teach that much lower concentrations of nalmefene are required to enhance analgesia than with either naloxone or naltrexone, thus further supporting that nalmefene optimizes dopamine homeostasis to a much greater extent than other opioid antagonists such as naloxone and naltrexone.

The prior art contains many examples of methods for prolonged delivery of naltrexone. Naltrexone implants, depots and other sustained release formulations of naltrexone have be described in great detail. These naltrexone preparations have been proposed as improved methodologies for treating addiction to opioid agonist analgesics. What has not been appreciated in the prior art are the unique pharmacological and clinical advantages provided by the prolonged administration of nalmefene via sustained delivery formulations such as sustained release formulations for per os administration, subcutaneous implants, injected depot preparations for subcutaneous or intramuscular administration and transdermal delivery systems.

A significant problem in treating humans addicted to opioid agonist analgesics with per os naltrexone is the significant gastrointestinal upset which is often caused soon after per os administration of this drug. Thus, to encourage use of opioid antagonists for addiction treatment, it is important to formulate a delivery system of opioid antagonist that is administered in other than per os form. Such a delivery system would tend not to dissuade a human from being administered an opioid antagonist, even if it were not in a sustained delivery formulation. Examples of such delivery routes are buccal, intranasal, sublingual, transdermal and transmucosal preparations, including suppositories for rectal administration. These routes of delivery, even if not delivered over a very prolonged time, still would increase patient compliance with opioid antagonist administration by allowing a third party to administer, or to observe self-administration, of the opioid antagonist. For example, a "squirt" through the nares and onto the nasal mucosa would ensure a delivered dose of antagonist. Further, by bypassing the gastrointestinal tract, such intranasal administration is much less likely to cause gastrointestinal upset. Intranasal administration has the further advantage, as does sublingual administration, of bypassing metabolism by the liver upon initial administration. Metabolism of a drug by the liver after delivery to the gastrointestinal tract is generally referred to as "first pass metabolism," and is a significant disadvantage for per os administration of many drugs. Nalmefene and naltrexone are two drugs that undergo very significant first pass metabolism. Of these two drugs, nalmefene is very much preferred for the treatment of opioid addiction because of its unique opioid receptor subtype binding profile compared to naltrexone, as described above.

The administration of opioid antagonists cause upregulation of opioid receptors present on the surface of cell of the central nervous system. The result of this increased density of opioid receptors is that more opioid receptors will then be available to the naturally occurring endogenous endorphins that are in proximity to these receptors. Because beta-endorphin production is decreased by a mechanism generally known as "negative feedback inhibition" in humans who are chemically dependent upon, and who are still being administered, exogenous opioid agonist analgesics, immediately upon cessation of opioid agonist analgesic administration there is a lack of beta-endorphin in these humans relative to the normal state in humans not chemically dependent upon opioid agonist analgesics. Thus, administration of opioid antagonists not only increase the number of receptors for beta-endorphin to bind to, in addition, these antagonists actually stimulate the production of endorphins by causing the release of negative feedback inhibition of its production. Thus, the cellular changes induced from chronic use of opioid agonist analgesics are reversed to a significant extent. Beta-endorphin attaches to and activates mu-opioid receptors, which results in a cascade of biochemical reactions, the result of which is an increase in central nervous system (CNS) dopamine. These changes brought upon by treatment with an opioid antagonist, such as nalmefene, restore to a human being a more normal physiological state, which will decrease the human's cravings for, and reduce the human's tolerance to, exogenously administered opioid agonist analgesics.

This upregulating effect of opioid antagonists in humans for treating addiction to opioid agonist analgesics has not been appreciated by those skilled in the art, particularly in the case of nalmefene which provides distinct pharmacological and clinical advantages over other opioid antagonist for treating addiction to opioid agonist analgesics. Nalmefene tends to optimize CNS dopamine by virtue of its greater affinity for kappa-opioid receptors relative to mu-opioid receptors, as compared to naltrexone and other opioid antagonists.

A sufficiently high concentration of opioid antagonist must be present at the opioid receptor blocked, e.g. at a $mu_1$-opioid receptor, to prevent an exogenously administered opioid agonist analgesic or its metabolite from binding to the receptoror, but not such a high concentration as to totally block binding of endogenous beta-endorphin to that receptor. Again, nalmefene is the unique opioid antagonist which will block beta-endorphin at $mu_1$-opioid receptors to a relatively lesser extent than other antagonists such as naloxone and naltrexone, while at the same time having optimal blocking of kappa-opioid receptors by endogenous molecules such a dynorphins. Therefore, nalmefene alone, as compared to naloxone and naltrexone, not only optimizes dopamine regulation during detoxification, but also following detoxification. Thus, nalmefene is not an analogous compound to other opioid antagonists because nalmefene provides distinct pharmocological and clinical advantages for post detoxification treatment of patients addicted to opioid narcotics not available with other opioid antagonists.

SUMMARY OF THE INVENTION

The present invention comprises methods of administering the medicinal agent nalmefene, with or without co-administration of a centrally-acting dopaminergic drug such as bupropion. In one aspect, the invention provides a method for administering nalmefene which acts to produce a prescribed serum concentration of nalmefene over some time period that optimally regulates dopamine release in the central nervous system. In a second aspect, the invention provides a method for administering nalmefene which bypasses the gastrointestinal tract and therefore eliminates "first pass" liver metabolism and also avoids gastrointestinal discomfort. In a third aspect, the invention provides a method of administering nalmefene which results in a relatively gradual release of nalmefene over time when administered enterally so as to avoid large peaks in serum nalmefene concentration after per os administration.

The pharmacological and clinical advantages provided by these methods can only be achieved using the opioid antagonist nalmefene. As discussed above, nalmefene alone, in stark distinction from other opioid antagonists such as naloxone and naltrexone, has unique binding affinities for opioid-receptor subtypes, namely mu-receptors and kappa-receptors. The unique binding profile of nalmefene allows for preferred blocking at kappa-receptors relative to mu-receptors, such that dopamine release will tend to be less inhibited due to actions at kappa-receptors than would be the case with equivalent blocking at mu-receptors by other opioid antagonists such as naloxone or naltrexone.

DETAILED DESCRIPTION OF THE INVENTION

Humans addicted to opioid agonist analgesics, such as buprenorphine, codeine, fentanyl, heroin, meperidine, methadone, morphine, opium, oxycodone, sufentanyl, and many other drugs classified as opioid narcotics, have a very difficult time abstaining from self-administering these analgesics, especially after detoxification and during the process associated with detoxification that is generally known as "withdrawal." The present invention fulfills a long-awaited need to aid such humans so that addiction treatment for chemical dependencies on opioid agonist analgesics is greatly enhanced.

The invention encompasses a variety of methods for administering nalmefene that produce relatively constant release of nalmefene into the bloodstream of a human for a relatively prolonged or sustainable time. Thus, the serum concentration of nalmefene is less likely to have significant peaks and troughs over time as seen in association with intravenous bolus injections of nalmefene, or per os administration of nalmefene in a non-sustained release form.

The invention further provides for a practical way of accomplishing the above stated ends. For example, nalmefene can, and has been, administered by constant intravenous infusion in a post-surgical setting or following opioid overdose. However, this method has not been used as a method for addiction treatment. Further, intravenous infusion is cumbersome and not at all practical in ambulatory humans, especially those prone to opioid agonist analgesic addiction.

By stark contrast to a constant intravenous infusion of nalmefene, the present invention allows for nalmefene to be constantly absorbed into the bloodstream by way of very small capillaries found within living human tissue at prescribed constant rates, such as by diffusion through skin with transdermal delivery, by diffusion through fat with subcutaneous delivery—either by surgical implantation or needle injection into fatty tissue, by gradual absorption through the gastrointestinal tract in a sustained-release per os delivery method, by absorption through muscular tissue as with intramuscular injection, by absorption through mucosa as found in the gastrointestinal tract, or by diffusion through mucosal membranes as found in the sublingual area of the mouth or in nasal passages.

The following examples illustrate the present invention:

EXAMPLE 1

There are a variety of transdermal delivery systems known in the art which deliver an array of medicinal agents in a sustained and constant fashion. Examples are Androderm® and Testoderm® systems that deliver testosterone, Alora™, Climara®, Estraderm® and Vivelle® systems which deliver estradiol, Catapres-TTS systems that deliver clonidine, Duragesic® systems which deliver fentanyl, Deponit®, Nitro Dur® and Transderm-Nitro® systems that deliver nitroglycerin, Habitrol®, Nicotrol® and ProStep® systems which deliver nicotine, and Transderm Scop® that delivers scopolamine.

The ideal steady state plasma concentration of nalmefene for blocking the effects of exogenously administered opioid agonist analgesics at mu-opioid receptors, while simultaneously allowing beta-endorphin to bind to and activate mu-opioid receptors, and effectively blocking dynorphins at kappa-receptors, in humans addicted to opioid agonist analgesics, is from about 1 to about 3.7 ng/ml, most preferably between about 1.25 and about 2.5 ng/ml, such as 2.15 ng/ml. For a 70-kilogram (kg) adult (but not elderly) human, a sustained steady state plasma concentration for nalmefene of 2.0 ng/ml can be achieved by a transdermal delivery system in the following way.

Assuming an elimination constant (a.k.a. $K_e$) for nalmefene of 0.0642 $hr^{-1}$ (which is a value for $K_e$ that is furnished by a distributor of nalmefene), and assuming an average volume of distribution (a.k.a. $V_d$) for nalmefene of 8.6 liters/kg (which has been shown to be an approximate average $V_d$ in non-elderly adult humans for nalmefene), a target serum concentration in a 70 kg adult of 2.0 ng/ml nalmefene can be maintained by administering parenteral nalmefene, as administered transdermally, at an input rate of approximately 1.8 to 2.0 mg per day.

2.0 mg/day nalmefene can be effectively administered transdermally by constructing a transdermal delivery system described as follows: FIG. 1 illustrates a transdermal delivery system as taught by the present invention. The system is embodied in a transdermal patch, generally designated 10, comprising drug reservoir 12 which includes a matrix 14 having nalmefene base and PEGML dispersed therethrough. The reservoir 12 is covered by a impermeable backing layer 16 which is sized slightly larger in circumference than the reservoir. An adhesive overlay 18 is provided for adhering the patch to the surface of the patient's skin. The overlay is separated from the reservoir 12 by the peripheral portion 20 of the backing layer 16 surrounding the reservoir 12. This is required to prevent adverse reactions between the PEGML dispersed in the reservoir and the adhesive supported on the overlay. The patch 10 further includes an adhesive release liner 22 which is removed by the patient or clinician just prior to attaching the patch to the skin.

A number of different materials are suitable for forming the matrix 14. However, due to the solubility characteristics of PEGML, the matrix is preferably formed from an anhydrous material such as natural or synthetic rubbers other polymeric materials, thickened mineral oil or petroleum jelly, when PEGML is used as the flux enhancing compound. In the illustrated embodiment, the matrix is formed from an ethylene vinylacetate copolymer preferably having an vinylacetate content of from about 28% to about 60%.

The nalmefene is dispersed through the matrix at a concentration in excess of saturation, with the amount in excess of saturation being determined based on the intended useful life of the patch. Accordingly, the typical concentration of nalmefene in the reservoir is in the range of from about 10% to about 35% by weight. The PEGML is dispersed through the matrix at a concentrations below saturation and preferably between the range of activity of from about 0.25 to about 0.60. Thus, the reservoir typically contains from about 25% to about 60% PEGML by weight. Where various PEGML compositions having different average molecular weights of the PEG component can be utilized, a composition comprising PEG (200–400) ML is preferred.

Figure 2:
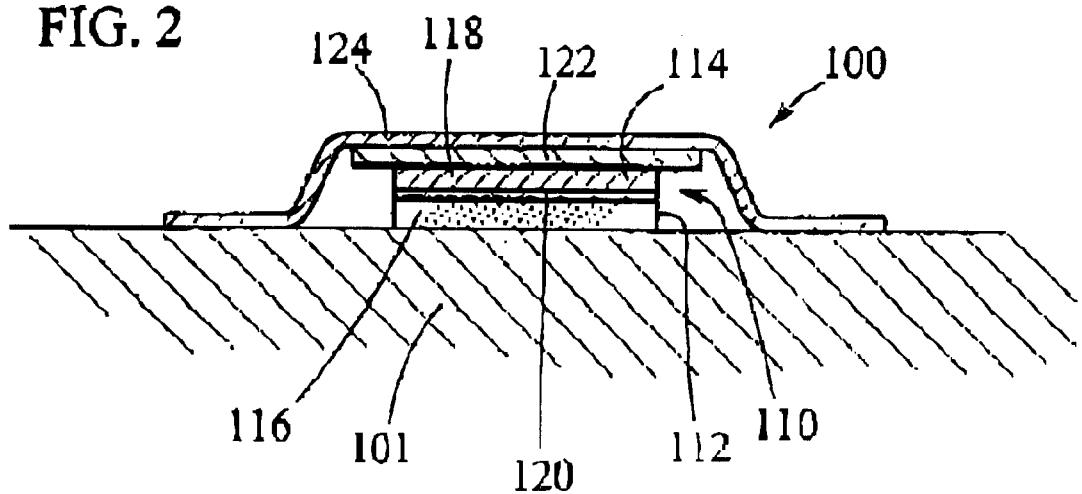

FIG. 2 illustrates a second embodiment of the transdermal patch. As shown in FIG. 2, the patch, generally designated 100, comprises a laminated reservoir 110 including layers 112 and 114. Layer 112 comprises a drug/flux enhancer reservoir substantially as described with respect to the reservoir 12 of FIG. 1. Thus, layer 112 includes as ethylene-vinyl acetate matrix 116 having nalmefene and PEGML dispersed therethrough. Layer 114 includes a PEGML reservoir that utilizes essentially the same matrix material 118 as that found in layer 112. The matrix 118 has PEGML dispersed therethrough but is substantially free of any undissolved nalmefene.

The patch 110 further includes a semi-permeable membrane 120 between layers 112 and 114 which controls the release of PEGML from layer 114 into layer 112 and from layer 112 into the skin. The membrane 120 may be formed from any pharmaceutically acceptable material having low permeability to PEGML, and in the preferred embodiment the membrane is formed from ethylene-vinyl acetate copolymer having a lower vinyl acetate content than the matrix.

The advantage of the FIG. 2 embodiment is that the nalmefene is concentrated in layer 112 near the surface of the skin, rather than throughout the entire reservoir as is the case with reservoir 12 in FIG. 1. This permits reduced loading of nalmefene in the patch, while at the same time providing for a sufficient PEGML reservoir for the intended life of the delivery system.

The patch 100 further includes an impermeable backing layer 122 superimposed over the reservoir 110 and an adhesive overlay 124 as described above with respect to the FIG. 1 embodiment. Also included is a release liner 126 that is removed just prior to attaching the patch to the skin.

To provide the desired plasma concentration of 2.0 ug/ml as described above, the patch is constructed, in one example, according to the FIG. 1 embodiment. The matrix is formulated with weight percentages of nalmefene and PEGML to provide an input rate of nalmefene of 20 ug/cm$^2$/hr. A patch having this input rate is dimensioned to present approximately 4.2 cm$^2$ of reservoir surface area in contact with the skin. Typically, the patch is configured to be substantially square-shaped, though it may be round, oval or of another shape having a similar area, and in a square formation measures approximately 2.05 cm×2.05 cm. In another example, the patch is formulated to deliver an input rate of 3.5 ug/cm$^2$ of nalmefene per hour. To provide the required plasma level, the size of the patch must be substantially larger. A patch of this type is dimensioned to present 23.8 cm$^2$ of reservoir surface area in contact with the skin. A circular embodiment of this patch is configured as a circle having a radius of approximately 2.8 cm, and it is significantly larger than the previously described example. With either of these examples, steady state nalmefene concentrations can be reached faster by giving a loading dose of nalmefene, e.g. by intravenous bolus as in rapid opioid detoxification under anesthesia Thus, the present invention is an extension of U.S. Pat. No. 5,783,583, which describes loading a human with nalmefene under anesthesia, then following the loading dose with a constant delivery of nalmefene.

To maintain a steady state plasma concentration of nalmefene of 2.15 ng/ml in a 80 kg human being, assuming a Vd of 8.6 L/kg and a Ke of 0.0642 hr$^{-1}$, a patch delivering an amount of nalmefene of approximately 2.3 mg per 24 hour period can be formulated as having an area of about 9.6 cm$^2$ if the percent by weight of nalmefene and flux enhancing compound is formulated to yield an input rate of nalmefene of about 10 ug/cm$^2$/hr. An embodiment of such a patch could be a circular patch with a diameter of about 3.5 cm.

As the foregoing demonstrates, the size and input rate of a prescribed series of transdermal patches can be individually altered to provide transdermal dosages of nalmefene consistent with the present invention. Alterations in flux enhancers and other materials making up the transdermal patch are likewise applicable to the present invention. Thus, upregulation of opioid receptors, stimulation of endogenous beta-endorphin release, and optimal blocking effects at both mu- and kappa-opioid receptors by nalmefene, which all serve to optimally regulate dopamine release, can be accomplished without it being necessary for the patient to return to the clinic daily over the extended term of a nalmefene maintenance program.

Additional advantages result from the continuous and sustained nature of transdermal delivery of nalmefene. Because the drug becomes absorbed into the dermis, removing a transdermal patch does not instantaneously stop drug administration. The lag between the time the patch is removed and the time the drug ceases to be absorbed into the bloodstream is an effective tool against the compulsive behavior that is typical of opioid addicted humans who seek immediate gratification from their actions. If an addicted human wanted to stop nalmefene delivery in order to experience the effects of exogenous opioid agonist analgesics, this would have to be planned out in advance by removing the transdermal delivery system some time ahead of the anticipated drug use. Thus, impulsive actions on the part of the addict would not result in immediate results. Such a lapse, in many instances, is sufficient to deter the addicted human from impulsively discontinuing nalmefene therapy. In addition, the removal of the patch by the patient is quite apparent to the support person or clinician monitoring the patient, thus making the process of monitoring easier and more effective.

It may be the case that the dosage schedule over the course of a nalmefene maintenance protocol will have to be tailored for each individual patient. The transdermal delivery system of the present invention is ideally suited for individualized dosage regimens since the size, delivery rate and number of patches can be readily designed to meet the needs of a particular patient. Variations among patients include mass (weight in kilograms), volumes of distribution, and the particular state of opioid receptor regulation at a given time.

The transdermal delivery of nalmefene in an appropriate dosage negates the effects of exogenously administered opioid agonist analgesics while maintaining the effects of the natural opioid endorphin system to the greatest degree possible. The constant delivery of nalmefene results in relatively constant serum concentrations, so as not to result in high peaks of nalmefene concentration as occurs following a bolus administration of the drug. This is especially important in treating addiction to opioid agonist analgesics, because if a high peak concentration of nalmefene is reached after each bolus, the concentration of nalmefene at mu-opioid receptors may become high enough to block not only exogenous opioid agonist analgesics, but naturally occurring endorphins as well. This would be expected to result in dysphoria or other unpleasant effects. Such unpleasant effects, if repeatedly associated with being administered nalmefene, may result in the development of an aversion to being administered the drug. This dissuades the human from being compliant with a prescribed regimen of nalmefene administration. Humans addicted to opioid agonist analgesics are notoriously unreliable in following a regimen of self-administer medications per os. Thus, transdermal delivery of an antogonist can provide important advantages with respect to patient compliance, since addicted humans will exhibit a much higher compliance rate for the full term of the nalmefene maintenance protocol.

While it may be necessary for patients to periodically replace a number of transdermal patches to complete a nalmefene maintenance protocol, this can be accomplished under the supervision of a support person designated to assist in, and to monitor, the treatment of the addicted human. Monitoring can be facilitated by placing the transdermal patch on the surface of the patient's skin and marking the edge of the impermeable backing layer and a corresponding portion of the skin surface in one or more locations with indelible marker. Marking the patch and the skin in this manner registers the patch with the skin, such that if the addicted patient removed the patch it would be difficult for him or her to replace it with the patch in the exact orientation prior to removal. Using this method, addicts can easily be monitored since the support person or a clinician can readily determine if the patch had been left in place.

EXAMPLE 2

Another way of delivering nalmefene both enterally in small incremental doses (as with normal swallowing) and parenterally (due to absorption sublingually) over a relatively prolonged period is to formulate a chewing gum preparation, such as nalmefene polacrilex, in a fashion somewhat resembling nicotine polacrilex which is marketed as Nicorette gum by SmithKline Beecham.

By formulating a nalmefene polacrilex gum with a given mass-unit of nalmefene per individual unit of chewing gum, the prescribed number of units of chewing gum can be administered to a human per over a prescribed amount of time to yield the preferred serum concentration of nalmefene, the prescribed number of units of gum per time-unit depending upon the lean body mass of a particular human.

EXAMPLE 3

Sustained administration of nalmefene may also be accomplished by surgically implanting an osmotic pump. The Alza Corporation manufactures osmotic pumps; one example is the surgically implantable ALZET® Osmotic pump, and another example is the OSMET osmotic pump for rectal administration. Both are capable of delivering nalmefene within the scope of the present invention.

For example, if the desired parenteral input rate into a human is 2.4 mg/day, then using ALZET® Osmotic Pump model #2ML1 that delivers liquid at a rate of 10 microliters (ul) per hour, or 240 ul/day, if the concentration of nalmefene is 10 mg/milliliter (10 mg/cc), the desired input rate can be achieved. To thwart local tissue immunological reactions and pump "encapsulation," a small dose of triamcinolone may be included in the osmotic pump for release to local tissue surrounding the implanted pump. In order to avoid subjective discomfort due to this foreign object being implanted subcutaneously, a pharmacologically compatible local anesthetic may also be included within the pump.

The particular osmotic pump embodied herein is described for illustrative purposes only, and is not intended to limit the scope of the present invention, which is consistent other osmotic pump release devices.

EXAMPLE 4

Nalmefene may be prepared as nalmefene polistirex, in a fashion similar to the known preparation of dextromethorphan polistirex. Such a form of dextromethorphan polistirex is manufactured by Mediva Pharmaceuticals, Inc. in Fort Worth, Tex. and is marketed as Delsym®, which provides an extended release of dextromethorphan over approximately 12 hours.

The preferred dose of nalmefene polistirex is based on the lean body mass of the treated human. By formulating an elixer of nalmefene polistirex with a given mass-unit of nalmefene per volume-unit, the prescribed amount of nalmefene can be administered that results in the preferred serum concentration of nalmefene.

EXAMPLE 5

There are a variety of intranasal delivery systems in the prior art that deliver various medicinal agents in a parenteral, non-intravenous fashion via absorption through the nasal mucosa Examples are Atrovent® nasal spray that delivers ipatropium bromide, Flonase® nasal spray which delivers fluticasaone propionate, Stadol NS® which delivers butorphanol tartrate, Beconase AQ® nasal spray that delivers beclomethasone dipropionate monohydrate, Nicotrol®NS nasal spray which delivers nicotine, Miacalcin® nasal spray which delivers calcitonin-salmon, DDAVP® nasal spray which delivers desmopressin acetate, Nasacort® AQ nasal spray and Nasacort® nasal inhaler which deliver triamcinolone acetonide, Nascobal™ gel that delivers cyanocobalamin, and Astelin® nasal spray which delivers azelastine hydrochloride.

According to the present invention, nalmefene is prepared as a free base or in its salt form and incorporated into a pharmacologically suitable nasal carrier, in a manner known to those skilled in the art. The choice of suitable carrier will depend upon whether the route of administration is by nasal solution, nasal suspension, or nasal aerosol using a volatile propellant. Generally, water is used in formulating a preparation, and the pH of the preparation may be altered by any one of known pH adjusters, e.g. sodium hydroxide.

A tartrate, stearate or palmitate formulation of nalmefene may be used, or nalmefene may be in the form of nalmefene hydrochloride, and formulated such that 1 gram of active nalmefene is mixed with 80 ml of distilled water, then adjusted to a pH of approximately 7.4 with dilute sodium hydroxide, and then isotonic saline is added along with a suitable preservative and antibacterial agent, to yield a total volume of 100 ml. This yields a nalmefene solution with a concentration of 10 mg/ml nalmefene. This final solution is passed through a 0.2 micron Millipor filter to remove bacteria and other undesired particles. The filtered solution is then placed aseptically into a container to which is then attached a metered dosing mechanism which allows approximately 0.1 ml to be delivered in each spray. An example of such a metered dosing system in found with the commercially marketed Stadol NS® (Bristol-Myers Squibb Co.). One spray to one nostril may be expected to yield a blood serum concentration of approximately 1 ng/ml 30–90 minutes after administration. Because the serum half life of nalmefene is approximately 10.8 hours, 5 consecutive 1 mg doses approximately 11 hours apart will result in steady state serum concentrations of nalmefene of approximately 1 ng/ml. Alternatively, the human may be given a loading dose of intravenous nalmefene and then transferred to a nasal administration regimen. A practical dosing schedule for nalmefene may be 1.5 mg intranasally every 12 hours. To facilitate this dosing regimen, 1.5 g of nalmefene may be substituted for the 1.0 mg previously described for preparation of a nasal solution, thus yielding a final concentration of 15 mg/ml, which can be administered in 0.1 ml increments.

In addition, permeation enhancers may be added to the nasal solution to increase input through the nasal mucosa. Palmitoyl and stearyl components of lysophosphatidylcholine in 0.5% concentration, are examples of mucosal permeation enhancers. Lysolecithin is a very potent mucosal permeation enhancer.

It is understood that these examples are for illustrative purposes only and are not to be construed as limiting the invention in spirit or scope.

EXAMPLE 6

Propellant-based aerosol systems for immediate non-intravenous parenteral delivery of a medicinal agent through oral mucosa sublingually are known in the art. For example, Nitrolingual® spray delivers nitroglycerin, which circumvents first-pass liver metabolism. This formulation utilizes dichlorodifluoromethane and dichlorotetrafluoroethan as propellants. Like propellants can be used in an aerosolized formulation of nalmefene which would be concentrated to deliver a dosing regimen similar to that described in Example 5. The manner of preparing a suitable formulation would be apparent to one skilled in the art in light of the present invention.

EXAMPLE 7

There are a variety of depot preparations for subcutaneous or intramuscular injection which provide for sustainable delivery of medicinal agents at a relatively even rate. These may employ particular methods that vary from one depot system to another. Examples include Lupron Depot® systems that deliver leuprolide acetate, Depo-Provera® that delivers medroxyprogesterone acetate and Zoladex® which delivers goserelin acetate.

The method for a sustainable releasing formulation of nalmefene, which is easily parenterally injected into subcutaneous or muscular tissue, may be as simple as preparing nalmefene in an oil base such as sterile peanut oil. More elaborate systems allow for a more controlled rate of release such that steady state serum concentrations of nalmefene are more constant. These systems may entail putting microencapsulated particles of nalmefene into a suspension that can then be delivered through a percutaneous needle. For instance, a polymer of a natural compound or compounds, such as a polymer or copolymer which includes biodegradable poly-lactic and poly-glycolic acids, polylactic acid, polyglucolic acid, polylactones, or any of a number of biodegradable non-toxic polymers, is used to encase or encapsulate particles of nalmefene. Poly(L(+)-lactic acid) and DL-lactic acid have been used in the prior art for sustained release drug formulations. These "microcapsules" are then suspended in a carrier solution. After being injected parenterally, preferably by subcutaneous route, the microcapsules break down over time thereby releasing active nalmefene for capillary absorption into the bloodstream. By varying the ratio of polymers in a copolymer, or by using different polymers or copolymers in a given suspension, and by varying the size of the microcapsules, the nalmefene can be released "in waves" from the suspension. In light of the present invention, one skilled in the art would be able to formulate a particle size of nalmefene, a microcapsule of the required size and composition, such that nalmefene would be released in a sustainable fashion while yielding relatively constant steady state serum concentrations of nalmefene consistent with the present invention.

As noted above, inclusion of a steroidal anti-inflammatory agent, e.g. triamcinolone, and a pharmacologically compatible local anesthetic, may provide the added benefits of greater comfort to the human administered the composition, as well as providing a means to decrease local tissue inflammatory responses which may cause induration or pain at the injection site.

EXAMPLE 8

There exists in the prior art a variety of surgically implantable delivery systems, one such example is the Norplant® system that delivers levonorgestrel. Grossman et al in U.S. Pat. No. 5,633,000 ('000) teach a subcutaneous implant comprising a poly(ethylene-vinyl acetate) matrix in which active drug is embedded. Nalmefene is not an equivalent drug to the active drug in claimed in '000. Further, the preparation of '000 is alleged to be "non-inflammatory, biocompatible and non-biodegradable," which therefore results in a prolonged, controlled release of active drug with "near zero-order" kinetics.

EXAMPLE 9

The prior art shows many sustained- or controlled-release tablets and capsules for per os administration. The oral controlled-release system is often made of polymers that release active drug by diffusion, bio-erosion, or swelling due to increased osmotic pressure generated in the gastrointestinal tract. Diffusion controlled systems contain a reservoir, matrix and porous membrane.

One method for producing sustained delivery of oral medications is to encapsulate active drug with slowly dissolving polymeric materials. The rate of release of active drug is influenced by the thickness and the dissolution rate of the particular polymeric coat of the active drug. By varying the thickness and dissolution rates of coated drug particles in a particular preparation, active drug will be released at different predetermined times. This is generally known as microencapsulation.

Another method for producing sustained or controlled delivery of orally administered drug is the matrix dissolution method. A means for preparing a drug-polymer matrix is "congealing" where the drug is mixed with polymeric substances or waxes. A specific method of congealing is known as "spray-congealing." Another means for matrix preparation is the aqueous-dispersion method. In this method, the drug-polymer mixture is sprayed or placed in water and then collected.

EXAMPLE 10

A hybrid of oral administration and osmotic pump delivery is the OROS® system developed by Alza Corporation. In this method, a non-digestible capsule is made of a semi-permeable membrane. Within the confines of this membrane is an osmotic core containing the active drug. As water passes through the semipermeable membrane due to an osmotic gradient, the water tends to push the active drug through an orifice in the capsule. This provides for constant delivery of active drug as the capsule passes through the gastrointestinal system. An example of this system is Acutrim®, which releases phenylpropanolamine in a sustained dose that causes appetite suppression but which produces little, if any, adrenergic-like side effects which typically accompany phenylpropanolamine administration by less controlled bolus administration.

Such non-digestible per os administration of nalmefene may provide a relatively easy solution to sustained action and controlled release of nalmefene consistent with the present invention.

EXAMPLE 11

Bupropion is co-administered with any of the above examples of nalmefene administration. When administered orally, a sustained release of bupropion is preferred, such as Wellbutrin®SR or Zyban®. Bupropion may be administered in a variety of delivery systems as previously described for nalmefene. A preparation combining the two active drugs nalmefene and bupropion may also be formulated. However, the simple co-administration of an orally administered sustained release tablet of bupropion HCL with nalmefene is suitable for optimizing dopamine release in the central nervous system in the setting of partially blocked mu-opioid receptors.

The invention also provides a method for sterilizing the above-described sustained-release delivery systems. The method comprises exposing a system to sufficient xray radiation to destroy any contaminating microorganisms, without causing any harmful effects to either the active ingredients contained in the sustained-release delivery system or to the composition of the materials comprising the system.

While preferred embodiments have been shown and described, various modifications and substitutions may be made without departing from the spirit and scope of the invention. Accordingly, it is to be understood that the present invention has been described by way of example and not by limitation.

What is claimed is:

1. A transdermal preparation designed to input therapeutically active ingredients into the bloodstream, comprising, as a therapeutically active ingredient, nalmefene, or pharmaceutically acceptable salts thereof, in a concentration sufficient such that the transdermal preparation has an input rate when applied to the skin of about 0.025 mg/kg to about 0.029 mg/kg per day nalmefene, or pharmaceutically acceptable salt thereof.

2. The transdermal preparation of claim 1 further comprising as a flux enhancing compound polyethylene glycol monolaurate.

3. A transdermal preparation, comprising, as a therapeutically active ingredient nalmefene, or pharmaceutically acceptable salts thereof, in a concentration sufficient when applied to the skin to produce a steady state plasma concentration in the patent of about 1 ng/ml to about 3.7 ng/ml nalmefene.

4. The transdermal preparation of claim 3 wherein the concentration of nalmefene, or pharmaceutically acceptable salt thereof, is sufficient to produce a steady state plasma concentration of about 1.25 to about 2.5 ng/ml nalmefene.

5. The transdermal preparation of claim 3 wherein the concentration of nalmefene, or pharmaceutically acceptable salt thereof, is sufficient to produce a steady state plasma concentration of about 2.15 ng/ml nalmefene.

6. The transdermal preparation of claim 3, further comprising as a flux enhancing compound polyethylene glycol monolaurate.

7. A transdermal preparation, comprising, as therapeutically active ingredients, nalmefene and buproprion, or pharmaceutically acceptable salts thereof.

8. The transdermal preparation of claim 7, further comprising as a flux enhancing compound polyethylene glycol monolaurate.

9. A sustained-release preparation comprising as therapeutically active ingredients nalmefene and buproprion, or pharmaceutically acceptable salts thereof.

10. A transdermal delivery system for application to the skin of a patient, comprising:

(a) a drug impermeable backing layer;

(b) an adhesive layer;

(c) a drug permeable membrane, wherein the membrane is positioned relative to the backing layer so as to form at least one drug reservoir compartment between the membrane and the backing layer; and (d) nalmefene, or pharmaceutically acceptable salt thereof, within the drug reservoir compartment in a concentration sufficient such that the transdermal delivery system has an input rate when applied to the skin sufficient to produce a steady state plasma concentration in the patent of about 1 ng/ml to about 3.7 ng/ml nalmefene.

11. The transdermal delivery system of claim 10 wherein said drug reservoir further comprises a matrix formed from an anhydrous material.

12. The transdermal delivery system of claim 11 wherein the anhydrous material is selected from the group consisting of: a natural or synthetic rubber, mineral oil, petroleum jelly, ethylene vinylacetate copolymer.

13. The transdermal delivery system of claim 10 wherein said drug reservoir further comprises a matrix comprising ethylene vinylacetate copolymer having a vinylacetate content of from about 28% to about 60%.

14. The transdermal delivery system of claim 11 wherein nalmefene, or pharmaceutically acceptable salt thereof, comprises from about 10% to about 35% by weight of the material in said reservoir.

15. The transdermal delivery system of claim 11 further comprising polyethylene glycol monolaurate.

16. The transdermal delivery system of claim 15 wherein said polyethylene glycol monolaurate is found in the reservoir in an amount from about 25% to about 60% by weight.

17. The transdermal delivery system of claim 10 wherein said drug reservoir comprises at least a first layer and a second layer.

18. The transdermal delivery system of claim 17 wherein said first layer comprises a nalmefene-flux enhancer and said second layer comprises nalmefene, or pharmaceutically acceptable salt thereof.

19. The transdermal delivery system of claim 10 wherein the delivery system has an input rate of about 3.5 $\mu$g/cm$^2$/hr to about 20 $\mu$g/cm$^2$/hr of nalmefene or pharmaceutically acceptable salt thereof.

20. A transdermal delivery system for treating pain in a human patient, said transdermal delivery system comprising: an opioid analgesic in a therapeutically effective concentration and nalmefene, or pharmaceutically acceptable salt thereof, in a concentration sufficient to produce when applied to the skin a steady state plasma concentration in the patient of about 1 ng/ml to about 3.7 ng/ml nalmefene.

21. A method of treating human patients suffering from opioid addiction by applying a transdermal delivery system containing nalmefene to the skin of the patient and maintaining the transdermal delivery system in contact with the skin for a time sufficient to provide a steady state plasma concentration of from about 1 ng/ml to about 3.7 ng/ml nalmefene.

* * * * *